United States Patent [19]
Jacobs

[11] Patent Number: 5,401,467
[45] Date of Patent: Mar. 28, 1995

[54] WHOLE BLOOD METERING CUP

[75] Inventor: Merrit N. Jacobs, Fairport, N.Y.

[73] Assignee: Eastman Kodak Company, Rochester, N.Y.

[21] Appl. No.: 94,668

[22] Filed: Jul. 21, 1993

[51] Int. Cl.6 ............................................. G01N 21/00
[52] U.S. Cl. .................................. 422/58; 422/61; 422/100; 436/164
[58] Field of Search ........................... 422/58, 61, 100; 436/164

[56] References Cited

U.S. PATENT DOCUMENTS

| | | | |
|---|---|---|---|
| 603,673 | 5/1898 | Ansley | 210/247 |
| 1,067,610 | 7/1913 | Ibbeken | 210/247 |
| 3,495,926 | 2/1970 | Naz | 8/3 |
| 3,615,257 | 10/1971 | Frost et al. | 23/292 |
| 3,846,077 | 11/1974 | Ohringer | 23/259 |
| 4,033,723 | 7/1977 | Givner et al. | 422/61 |
| 4,214,993 | 7/1980 | Forsythe, Jr. et al. | 210/282 |
| 4,234,317 | 11/1980 | Lucas et al. | 23/230 B |
| 4,288,316 | 9/1981 | Hennessy | 209/17 |
| 4,636,361 | 1/1987 | Marian | 422/101 |
| 4,693,834 | 9/1987 | Hossom | 210/767 |
| 4,786,471 | 11/1988 | Jones et al. | 422/61 |
| 4,965,187 | 10/1990 | Tonelli | 435/5 |
| 4,978,504 | 12/1990 | Nason | 435/295 |
| 5,000,922 | 3/1991 | Turpen | 422/101 |
| 5,019,033 | 5/1991 | Geria | 604/2 |
| 5,084,245 | 1/1992 | Berke et al. | 422/61 |

*Primary Examiner*—Lyle A. Alexander
*Attorney, Agent, or Firm*—Dana M. Schmidt

[57] ABSTRACT

A method and related apparatus for the dispensing of a biological liquid, such as whole blood, to a diagnostic test element is described, in which a quantity of patient sample is preferably added to a container having contained filters for separating and supporting a quantity of the sample. The container has an exterior surface wettable with the filtered sample, a cover to prevent significant evaporation of the wetted filter surface, and a movable transfer element for transferring filtered liquid from the wetted surface and delivering the liquid to a test element.

8 Claims, 9 Drawing Sheets

WHOLE BLOOD METERING CUP

FIELD OF THE INVENTION

This invention relates to the field of clinical diagnostic analyzers and more particularly to a method and related apparatus for the filtering and transferring of a patient sample onto a test element.

BACKGROUND OF THE INVENTION

In the field of testing of liquid analytes, particularly those using the so-called dried chemistry technology, a quantity of patient liquid is dispensed onto a test slide element having at least one dried reagent layer with which the liquid interacts to produce a detectable signal for sensing the analyte of interest.

It has been required with clinical diagnostic analyzers, such as those manufactured by Eastman Kodak Company under the trademark "EKTACHEM TM", which use the dried chemistry assay approach, that serum be separated from the whole blood sample prior to testing of the sample. Techniques for performing the separation are known and typically require centrifugation of a liquid sample to separate the heavier phase, (e.g., that portion carrying the red blood cells), from the lighter phase, (e.g., serum). These separation techniques are expensive in that they require a centrifuge, or other apparatus, to perform the separation. In addition, these techniques are time consuming in that they are usually performed offline and separate from the analyzer prior to testing of the filtered sample.

Alternatively, there are known filtering techniques in which a quantity of patient liquid is added to one end of a filter and separated. The filtered liquid then directly passes into a container for holding the filtered liquid from where the liquid can be aspirated into a conventional pipette tip for metering onto a test element. Alternatively, the separated liquid may be retained at one end of the filter after being passed therethrough.

There are associated problems with each described technique. In the first described method, additional processing steps are required to first collect the filtered liquid and subsequently to aspirate it into a tip for dispensing. In addition, using multiple pipette tips and containers increases the number of disposables.

There are also a number of potential problems associated with the metering of a sample, filtered or otherwise, using conventional point source deposition methods.

In the most common point source method, the pipette tip approach, a predetermined quantity of liquid is dispensed from the orifice of a pipette tip suspended a short distance above the test element. The point source delivers the liquid in the form of a droplet which strikes the test element in a localized area. Biological liquids, such as serum, however, vary in terms of their spreadability (diffusivity) horizontally across a test element surface. For example, a patient sample having a higher concentration of lipids, or lipo-proteins, will not spread as easily as one with a lower concentration due to its higher viscosity. The inability to spread, and further the inability of some liquids to spread homogeneously, may produce inaccuracies in the detection of an analyte of interest.

The accurate dispensing of the liquid onto the surface of a test element is also dependent upon a number of other factors, such as adhesion of the liquid to the tip, flow characteristics of the tip nozzle, the distance of the tip from the test element, the air flow in the vicinity of the tip, etc. Spreading layers typically provided for in the chemistry portion of a test element provide for horizontal as well as vertical diffusivity across the dried reagent layer(s); however, it is possible that the spreading will not be homogenous. In addition, the manufacture of a porous spreading layer to horizontally distribute the sample droplet is expensive.

In the second filtering technique described above, there are also a number of associated problems. Firstly, a predetermined quantity of patient liquid cannot be dispensed directly from the wetted end of a filter without potentially flooding the test element. Typically, it is required for only about 10 $\mu$l of liquid to be dispensed to the test surface area of a test element. In addition, liquid collected at the wetted end of a filter is prone to excessive contact with the atmosphere causing some of the collected liquid to evaporate prematurely, and require an excess of biological liquid be used.

Therefore, there is a need to provide a method of directly providing whole blood or other unfiltered patient liquid to an analyzer wherein the whole blood can be separated and then transferred onto the test surface of a test element with a minimum of processing steps.

A further need is to provide a container for storing a patient sample from which a number of patient samples could be transferred to the surface of a test element without the need for additional disposable parts.

An additional need is to control the amount of dispensed volume to the test element from a container having filtration means so that a generally uniform and thin layer is transferred directly without the necessity for horizontally flowing the sample as required with point source metering.

RELATED APPLICATIONS

Reference is made to copending and commonly assigned application Serial Nos. U.S. application Ser. Nos. 08/094,724 08/094,722, filed Jul. 21, 1993 entitled: SURFACE AREA TRANSFER METHOD AND RELATED APPARATUS, and METHOD OF PRETREATING which are incorporated by reference.

SUMMARY OF THE INVENTION

Specifically, in accordance with the invention there is disclosed a method of filtering and dispensing a quantity of filtered liquid to a test element, comprising the steps of:

a) adding a liquid to a filter at one end of the filter;
b) causing the liquid to pass through the filter to an opposite end where the filtered liquid wets the opposite end;
c) temporarily closing off access to the wetted end by the atmosphere;
d) transferring some of the filtered liquid on the wetted end to an applicator, and
e) applying liquid on the applicator to a test element.

In another aspect of the invention, there is disclosed a container useful for filtering and dispensing of a biological liquid having an entrance opening and an exit opening, a filter disposed within the container and having a surface wettable with filtered liquid and adjacent the exit opening, in which the container further has closure means for closing off access of the wettable surface to the atmosphere comprising a cover section which is movably attachable to the container, and means on the cover section for transferring liquid from the wettable surface to a test element.

An advantageous feature of the invention is that no precise quantity of fluid is required to be aspirated or otherwise precisely delivered to the container; all that is necessary is that a quantity of fluid, sufficient to effectively coat a test element, be placed within the container.

A further advantageous feature of the invention is that use of a container as herein described allows multiple tests to be performed while using the same container, thereby reducing the number of disposables, and provides a cheaper and improved means for delivering filtered liquid to a test element.

Yet a further advantageous feature is that by delivering a quantity of liquid uniformly to the test surface area of a test element, without consideration of flow characteristics, a smaller quantity of liquid is required to effectively coat the test element and provide an adequate basis of detection, even in the extreme outer portions of the detection area.

A still further advantageous feature of the present invention is that a surface dispersed quantity, as defined below, can be delivered to the test volume of a test element all at once, providing a relatively constant concentration level of liquid across the detection read area without significant washout of the dried chemistry or transient liquid flow after delivery.

Other advantageous features will become apparent upon reference to the following Description of the Preferred Embodiments, when read in light of the attached drawings.

DETAILED DESCRIPTION OF PREFERRED EMBODIMENTS

The present invention is herein described in terms of the attached Figures. In the embodiments illustrated, reference is made to the terms "lower", "upper", "top", "bottom", etc. These descriptions are to more clearly describe the embodiments shown, but are not limiting to the views shown. In addition, the term "surface-dispersed quantity" means, a quantity in which the surface area/volume ratio is approximately 1:1, e.g., if a 10 microliter volume has a 10 mm$^2$ dispersed surface area and a 1 mm thickness, its ratio is 1:1. Ratios of 9:10 or 11:10 are included here.

Figure 1:
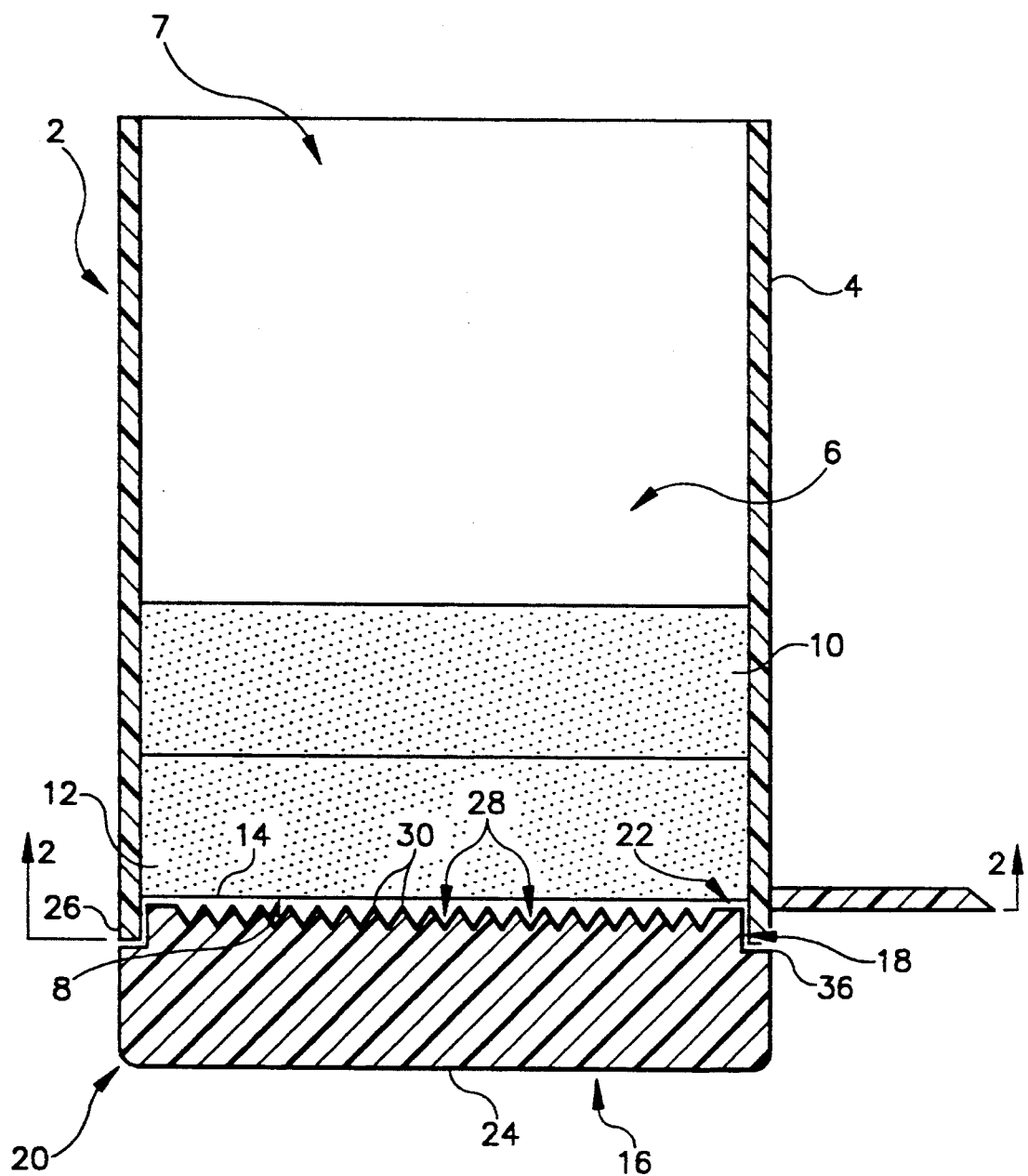
FIG. 1 is a side elevational view, taken in section, of one embodiment according to the present invention.

Referring to FIG. 1, there is provided a container, or cup 2, having sidewalls 4, and an interior portion 6. An entrance opening 7 is provided to allow liquid to enter container 2, as well as an oppositely disposed exit opening 8. Container 2 is preferably made from a lightweight plastic material such as polystyrene, though almost any liquid-impermeable material can be used.

In the embodiment illustrated, container 2 has a cylindrical configuration, defining a circular cross-section, although either the configuration and/or cross-section can be easily varied for convenience. For example, in another preferred embodiment, container 2 can be constructed such that sidewalls 4 taper inwardly from the top opening of the container, (not shown) thereby defining a conical configuration to provide a more stable structure, as well as a larger surface area for separation of a biological liquid.

Within interior portion 6 is at least one porous filter. In the embodiment illustrated, a first and a second filter, 10, 12, respectively, are provided, each preferably having a pore size of less than 3 microns, for allowing liquid material to migrate therethrough, while retaining larger particulate matter, such as separated red blood cells. Each filter 10, 12 is sized to fit within interior portion 6 and is made from glass microfiber or cellulosic material, though other porous materials capable of filtering biological fluids may be used. In addition, the size and number of filters required may be varied to account for a number of other configurations other than the one herein described; for example, a single filter may be utilized, or a series of filters, each having differing pore sizes.

Figure 2:
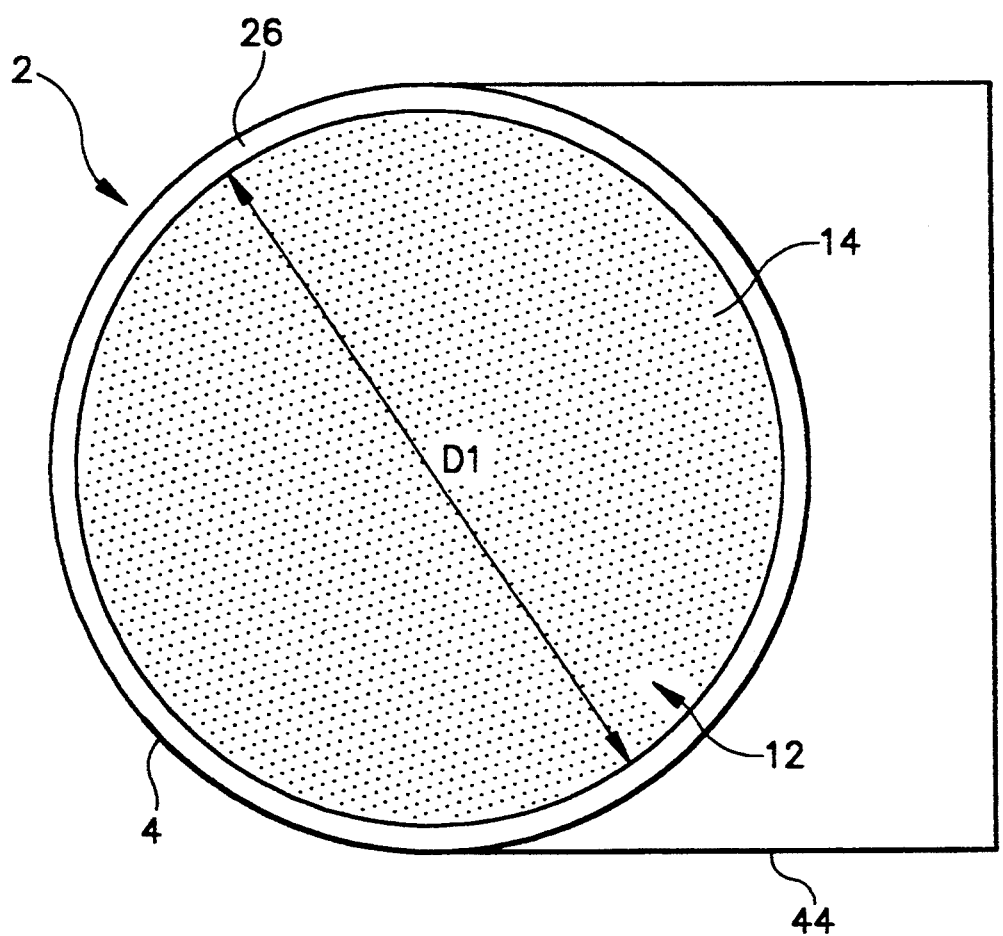
FIG. 2 is a bottom partial cross-sectional view of the container illustrated in FIG. 1 taken along the line 2—2.

Referring to FIGS. 1 and 2, second filter 12 is disposed directly beneath first filter 10 and has an exterior surface 14. Preferably, exterior surface 14 is recessed within exit opening 8, formed by lip 26 extending downwardly from sidewalls 4. Exterior surface 14 is capable of retaining filtered liquid and is preferably defined by a circular configuration having a diameter D1.

Movably attached to the bottom of container 2 and adjacent exit opening 8 is a cover, or cap 16, having a first and a second end 18, and 20, respectively. Second end 20 is preferably defined by a back, or posterior surface 24, while first end 18 is defined by a liquid supporting anterior surface 22.

Figure 3:
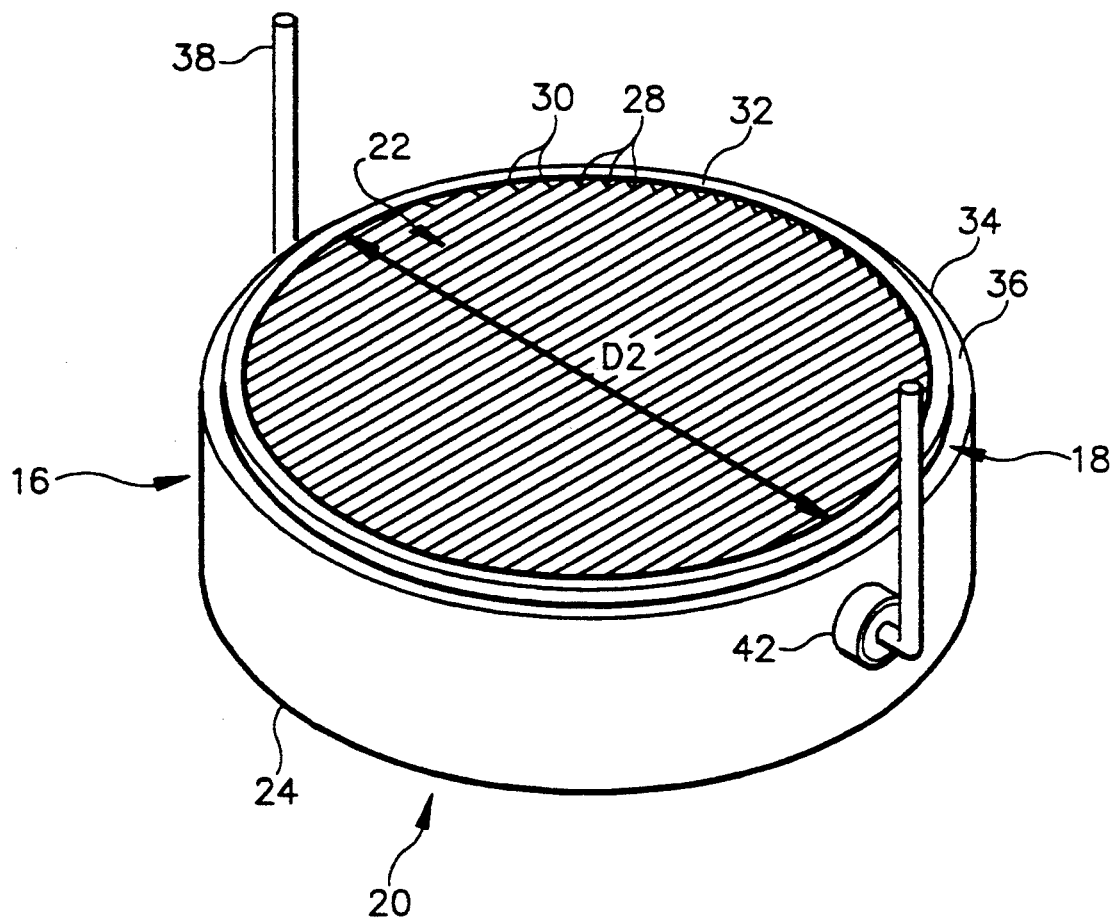
FIG. 3 is an isometric view of the cover portion of the container illustrated in FIG. 1.

Referring to FIGS. 1 and 3, first end 18 is defined preferably and substantially over the entirety of anterior surface 22 by a plurality of substantially parallel V-shaped grooves 28, as defined by equally spaced rib members 30. In the embodiment illustrated, each groove 28 is capable of supporting a quantity of liquid though alternate arrangements, with or without grooves, may be provided; for example, by providing grooves disposed in a diamond-like configuration, or by providing a textured surface (not shown) provided the surface is capable of supporting a liquid quantity thereon. In addition to the above, one or more equalization grooves, or cross-channels (not shown) can also be provided extending orthogonally to rib members 30 to avoid premature siphoning of liquid from surface 6.

Disposed circumferentially about grooves 28 is a relatively thin ring-like section 32, made from a material, such as polypropylene with minimal protein adhesion, though other liquid-impermeable materials such as polymethacrylamine or copolymers with other acrylic amides or esters may be used.

At the outer periphery 34 of first end 18, an annular edge 36 is provided which is recessed from surface 22 sufficiently so that when cover 16 is engaged with the remainder of container 2 surfaces 22 and 14 can be brought into contact with one another. Cover 16 is also preferably sized so that diameter D2, corresponding to anterior surface 22 is at least equal to diameter D1 of exterior surface 14. In the embodiment illustrated, D1 is equal to about 6 mm and D2 is equal to about 5 mm. A relatively good seal is therefore provided when cover 16 is engaged with the remainder of container 2, minimizing air contact with exterior surface 16, once attached thereto.

Along the exterior of container 2 and disposed above cover 16 and extending outwardly therefrom is a knife-edge 44 used to remove excess liquid material from the cover once liquid has been transferred to liquid supporting surface 22.

Figure 4:
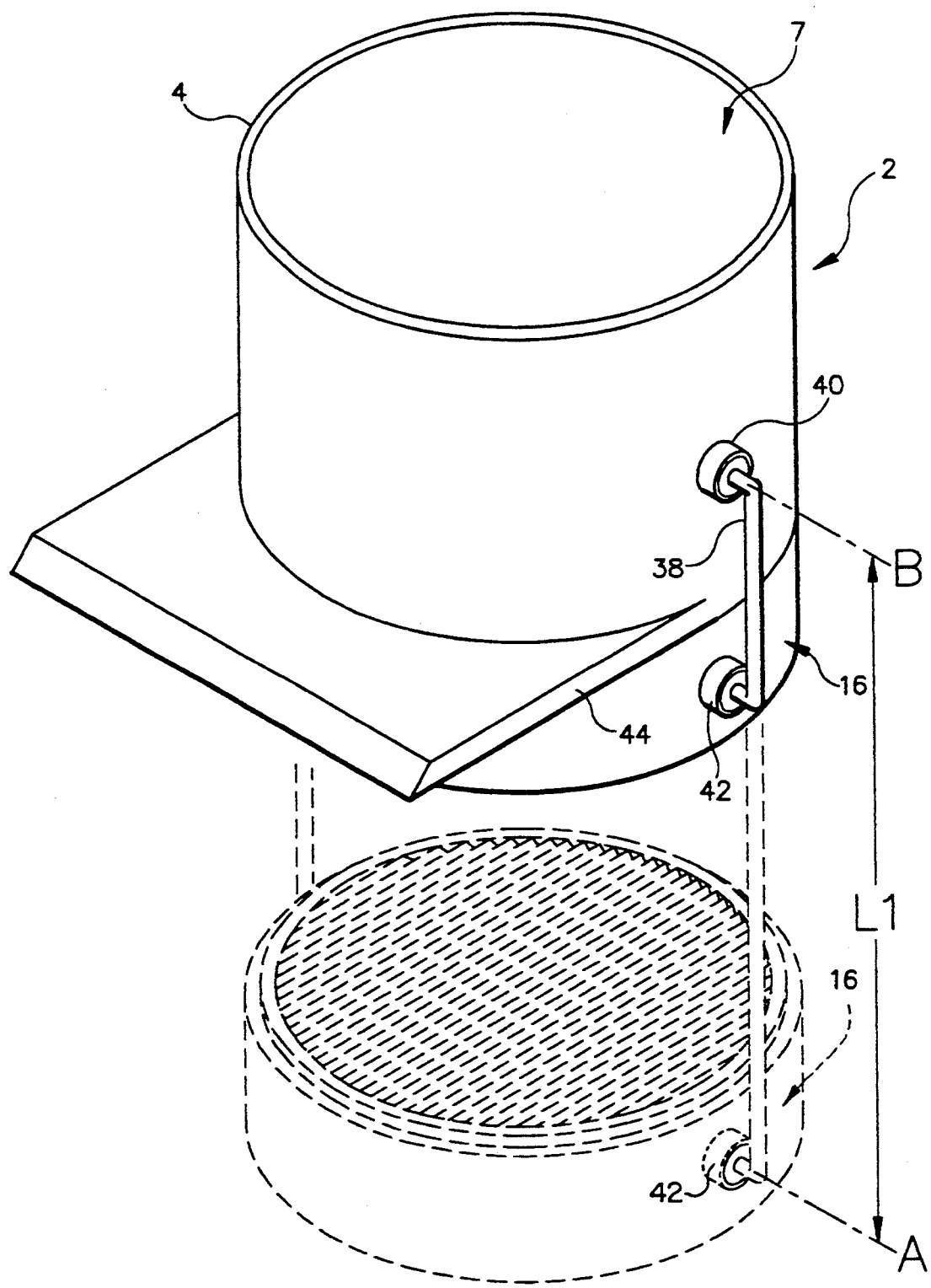
FIG. 4 is an isometric perspective view, rotated 90°, of the container shown in FIG. 1, showing the disengagement of the cover portion shown in FIG. 3.

Referring to FIGS. 3 and 4, cover 16 is movably attached to the remainder of container 2 by a pair of telescopic arms 38 oppositely positioned along the exterior of sidewalls 4. In the embodiment illustrated, arms 38 are pivotably mounted to cover 16 at mount 42, creating a first pivot axis -A-, and to sidewalls 4 at mount 40, creating a second pivot axis-B-. Each mount 40, 42 provides a bearing surface allowing cover 16 and arms 38, respectively, to rotate about axes A and B, though almost any form of pivoting means may be provided. By also allowing arms 38 to be extendable, adequate clearance is provided to allow cover 16 to be rotatable about pivot axis -A- when extended to length L1, FIG. 4, without contacting the remainder of container 2, while also allowing cover 16 to remain attached thereto. Other means for attaching to container 2, however, can be provided. Alternatively, cover 16 can be made fully removable from container 2 without the need for any attachment means.

One embodiment of the operation of the described container 2 is shown in FIGS. 5-9.

Figure 5:
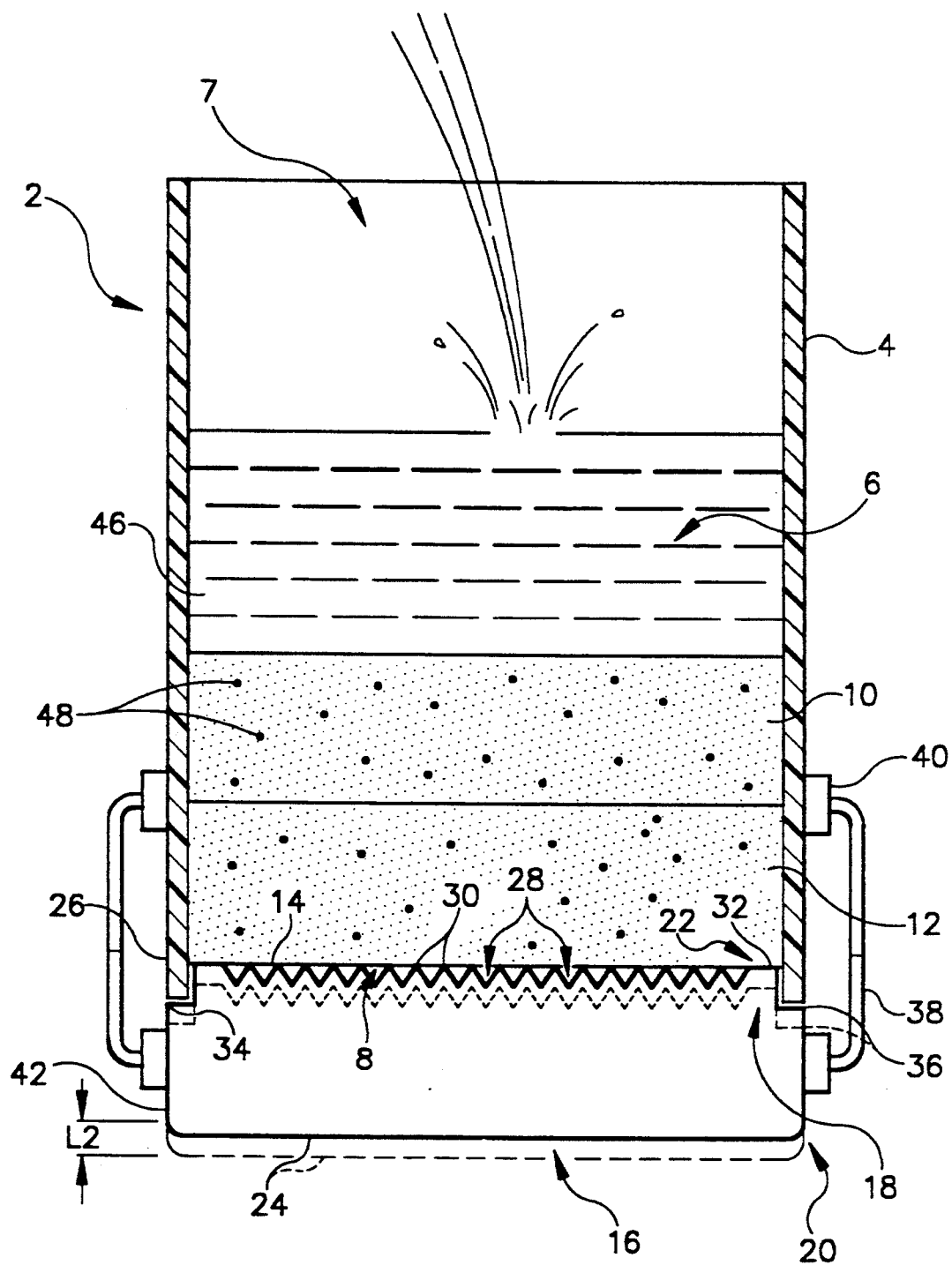
FIG. 5 is a side elevational view, shown partially in section, of the container illustrated in FIGS. 1-4 showing the filling of the container with a liquid to be filtered.

Referring to FIG. 5, a quantity of an unseparated biological liquid 46, such as whole blood, is added by any conventional dispensing means, such as by pipetting (not shown) to container 2. As liquid 46 migrates through interior portion 6, the larger and heavier constituents 48, such as the red blood cells, are trapped within the pores of filters 10 and 12, respectively, while the remainder, or lighter phase of the liquid, continues to migrate downwardly under the force of gravity. The pores in filters 10, 12 are sufficiently large for allowing filtered liquid 46 to pass therethrough, wetting porous exterior surface 14. Note that exterior surface 14, now glutted with filtered liquid 46, vertically expands along sidewalls 4 due to the corresponding increase in volume.

Preferably during the filling operation, cover 16 stays in contact with the remainder of container 2. This allows access to exterior surface 14 to be substantially closed to the atmosphere, preventing premature evaporation of filtered liquid 46 prior to transfer.

Cover 16 is then preferably disengaged a nominal vertical distance, L2, from the remainder of container 2, by extending telescopic arms 38. In the embodiment illustrated, L2 is roughly about 0.5 mm, FIG. 5, though the particular disengagement length is not critical.

Cover 16, is then reengaged with container 2 by retracting telescopic arms 38, thereby placing surfaces 14 and 22 respectively, into contact with one another, surface 14 now having been glutted with liquid. Disengaging and reengaging cover 16 as described allows air to be evacuated from grooves 28, thereby providing a site for transferring a portion of liquid 46 from wetted filter surface 14 to anterior liquid supporting surface 22. The small amount of air evacuated from grooves 28 is vented outward of container 2 at the edges between contacting surfaces 14, 22 in that the contact is not a perfect seal due to the porosity of filter material, though small vent holes (not shown) may be alternately supplied. Liquid migrating to anterior surface 22 adheres thereto due to surface tension in the form of a meniscus 52, FIG. 6.

Figure 6:
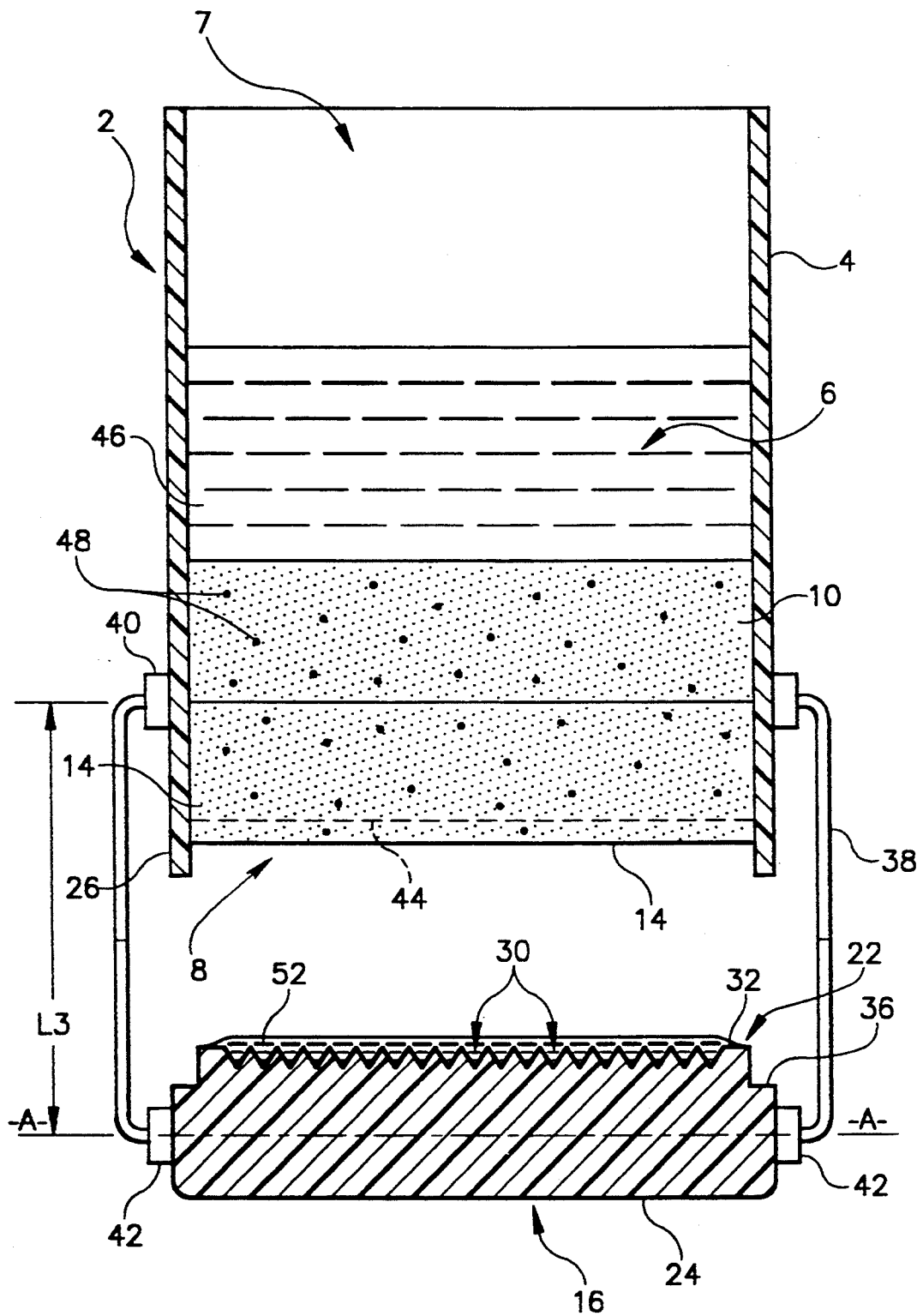
FIG. 6 is a side elevational view, shown partially in section, of the container shown in FIGS. 1-5 illustrating the disengagement of the cover portion after transfer of liquid has occurred.
Figure 7:
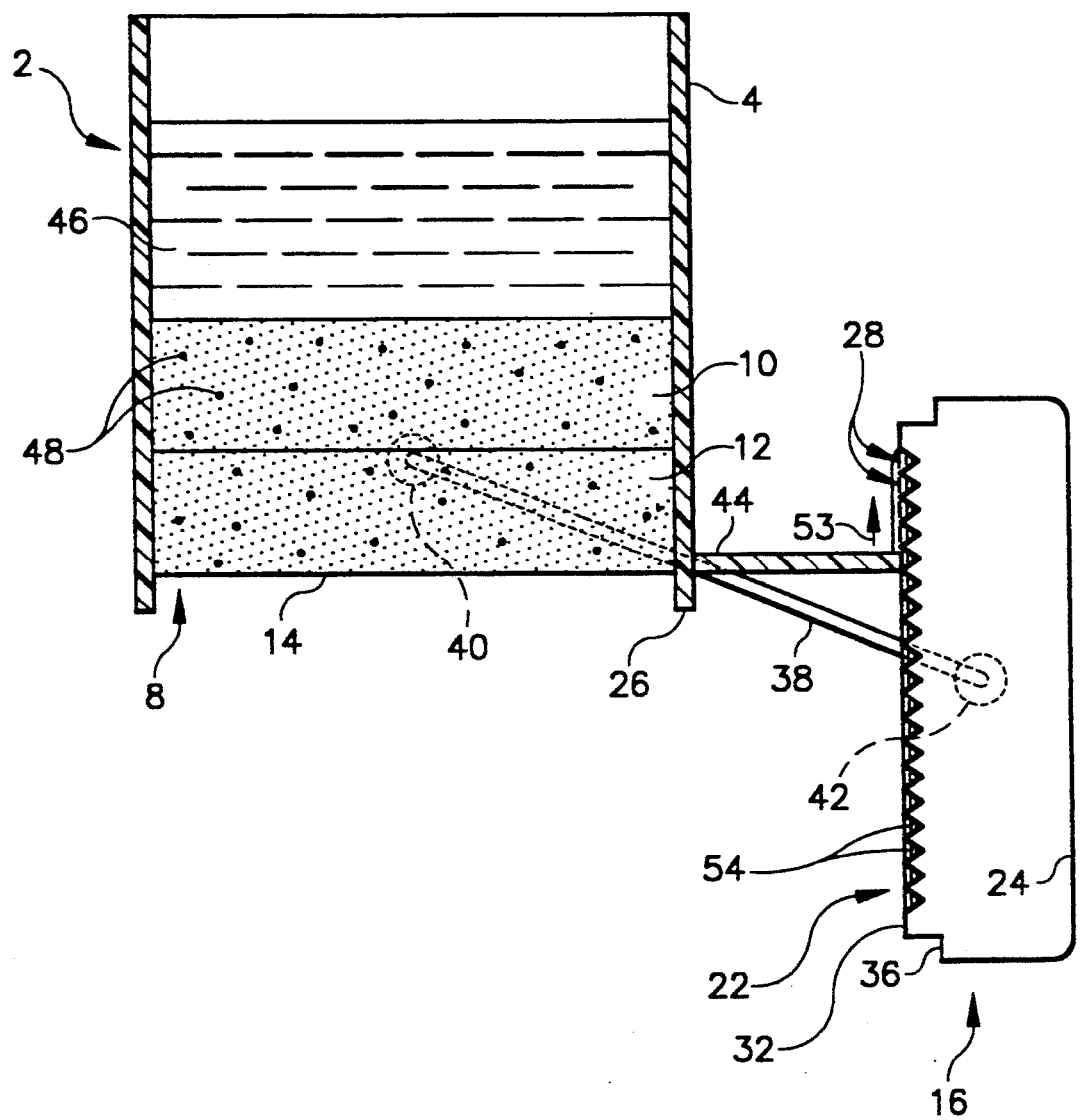
FIG. 7 is a side elevational view, shown partially in section, of the container illustrated in FIGS. 1-6 showing the removal of excess liquid material from the cover portion.

It is desirable to remove a portion of meniscus 52 prior to deposition of the liquid sample onto a test element, in order to avoid potential flooding of the element. Referring to FIGS. 6 and 7, cover 16 is extended a distance L3 from the remainder of container 2 by extending arms 38, FIG. 6, and is then pivoted about pivot axis -B- allowing cover 16 to be positioned alongside of knife edge 44, FIG. 7.

Liquid-supporting surface 22 is then drawn across surface of knife edge 44, per arrows 53, FIG. 7, by additionally pivoting arms 38 about axis -B- so that excess liquid in the form of meniscus 52 can be scraped away. The amount of liquid 54 remaining within grooves 28 following this operation, is preferably sufficient to coat the test surface area of a test element, FIG. 9. In addition to removing excess liquid, the energy supplied by drawing knife edge 44 against grooved surface 22 assists in removing any residual air pockets formed within grooves 28, allowing them to be filled with liquid 54 by capillary action. Note that other removal means, such as wicking using absorbant material or other scraping means may be used to remove the excess material.

Figure 8:
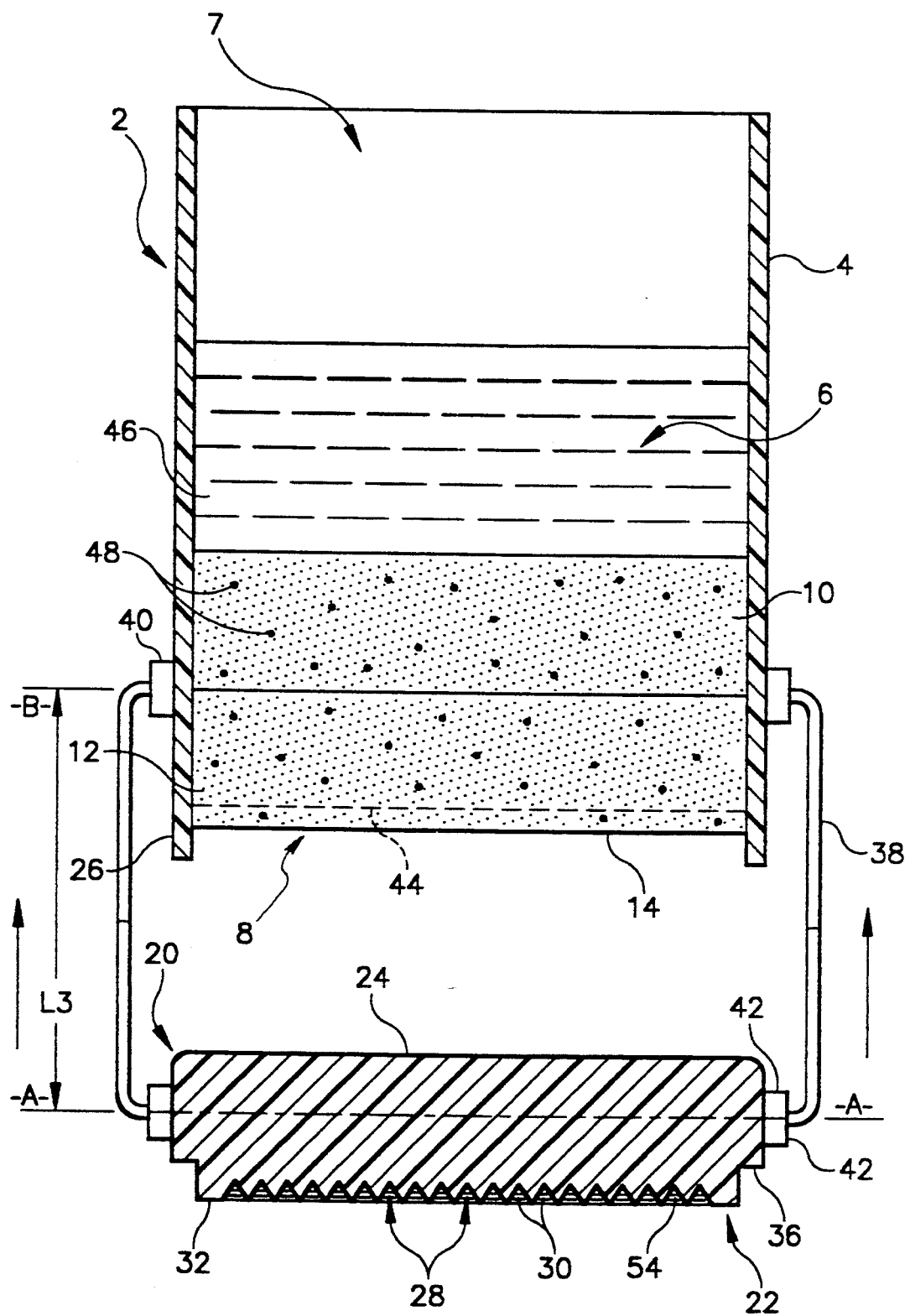
FIG. 8 is a side elevational view, shown in section, of the container illustrated in FIGS. 1-7 showing the orientation of the cover portion prior to the dispensing of liquid onto a test element.
Figure 9:
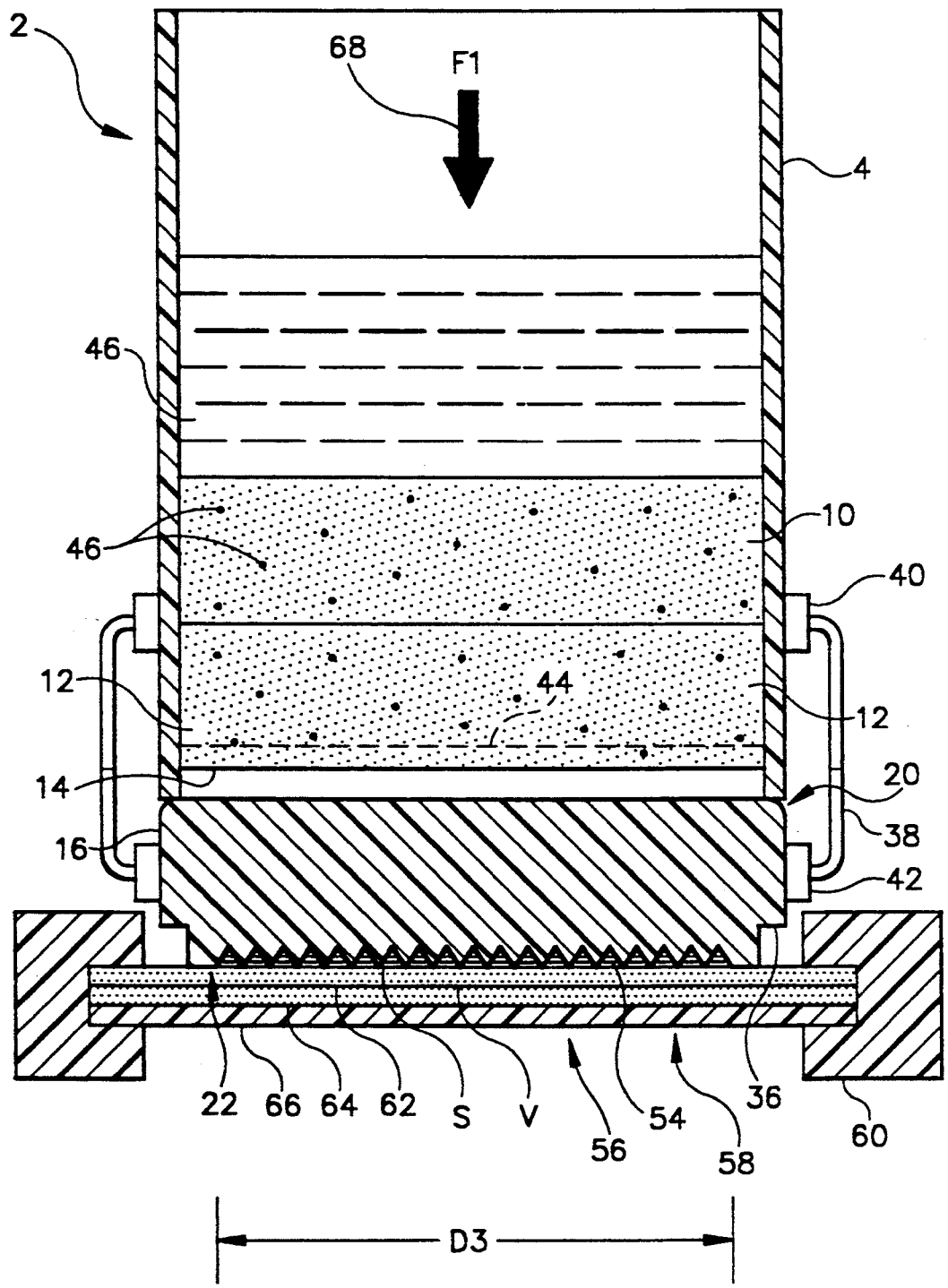
FIG. 9 is a side elevational view, shown in section, of the container assembly shown in FIGS. 1-8, illustrating the transfer of liquid onto a test element.

Referring to FIGS. 8 and 9, the still extended arms 38 are then pivoted about pivot axis -B-until cover 16 is positioned directly below the remainder of container 2, preferably at length L3. Cover 16 is then preferably rotated about pivot axis -A-until liquid-supporting, or anterior surface 22 is facing in a downward direction, or facing in a direction opposite to that of the remainder of container 2, for aligning with a test element 56.

Test element 56, FIG. 9, is defined by a support frame 60, and a chemistry portion 58 containing at least one dried chemistry reactant layer. In the embodiment illustrated, chemistry portion 58 is made up of a first top reactant layer 62 positioned above a second reactant layer 64, each being positioned upon a support 66. The top reactant layer can be a reagent layer, or alternatively be a spreading layer such as in U.S. Pat. No. 3,992,158. A test surface area S is defined within chemistry portion 58 having a diameter D3.

After cover 16 has been rotated to align it with test element 56, arms 38 are preferably retracted so that cover 16 is brought into contact with the remainder of container 2 to provide a more solid support. As noted above, expansion of exterior surface 14 has occurred due to liquid swelling within filter 12. By extending sidewalls 4 vertically as shown by lip 26, however, second end 20 will not contact the expanded exterior surface 14. Other alternate means of modifying either second end 20 or container 2 may be employed. For example, second end 20 could be designed with a recessed surface (not shown) to avoid contacting surface 14 when cover 16 has been rotated.

The entire assembled container 2 is then lowered by means (not shown) until grooves 28 are placed into compressive contact with chemistry portion 58. As a downward compressive force F1, shown by arrow 68, is applied, liquid 54 contained within grooves 28 is transferred directly and all at once to the test surface area S of test element 56. The surface area of liquid supporting surface 22 is preferably sized to be at least equal to test surface area S so that liquid can be transferred all at once to test element 56. In the embodiment illustrated, a compressive force F1 of about 0.5 oz. is adequate to transfer liquid 54 to test element 56 without damaging the fragile chemistry portion 58. Container 2 can then be lifted away from test element 56 by any convenient means (not shown), leaving surface area S wetted with liquid 37.

It can be seen that multiple tests can then be performed using a single container as described. Furthermore, by transferring a filtered liquid to the entirety of the test surface area of a test element as described, there is no further need for providing multiple disposable pipette tips.

In addition, it is not required that a predetermined amount of liquid be added to the container in that a specific amount of sample is delivered to the entirety of the test element, the amount delivered being dependent on the configuration of the liquid-supporting surface.

Furthermore, it should be apparent that literally any liquid could be transferred using a container and the method described herein. For example, a quantity of an already separated biological liquid, such as serum, could be added to the container wherein the filter could serve as a means for supporting a quantity of liquid to be transferred to a test element.

Another realized advantage is that the ability to transfer a volume of liquid uniformly and all at once to the entirety of a surface area as a surface-dispersed quantity to the test volume V of element 56 also negates the necessity for a horizontally diffusing spreading layer. Thereby, the manufacture of test slide elements, and in particular, the manufacture of the chemistry portion 58 contained therein is simplified.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. In a container useful for filtering and dispensing a biological liquid onto a test element, the container comprising an entrance and an exit opening, a filter disposed within the confines of said container, and having a surface wettable with said liquid and adjacent said exit opening, wherein the improvement comprises:

closure means for closing off access of said wetted filter surface from the atmosphere, said closure means comprising a cover section movably mounted to temporarily close off said container at said exit opening, and means on said cover section for transferring filtered liquid from said wettable surface to a liquid-supporting surface of said cover and then to a test element located external to said container, said liquid-supporting surface comprising a plurality of grooves extending over substantially the entirely of said surface.

2. A container as claimed in claim 1 wherein said liquid-supporting surface includes grooves arranged in a diamond-like configuration over said liquid-supporting surface.

3. A container as claimed in claim 1 further comprising attachment means for movably attaching said cover section to said container.

4. A container as claimed in claim 3 wherein said attachment means comprises means for rotating said transfer element so as to align the liquid supporting surface with a said test element and said wetted end.

5. A container as claimed in claim 1, wherein said transfer means comprises a transfer element and said surface is capable of supporting a quantity of filtered liquid thereon for transferring a surface-dispersed quantity all at once to the test surface area of a test element, said transfer element being movably attachable to said container.

6. A container as claimed in claim 5 wherein said cover section comprises said transfer element.

7. A container as claimed in claim 5 further comprising means for removing excess liquid material from said transfer element.

8. A container as claimed in claim 7 wherein said removal means comprises a knife edge disposed about the periphery of said container.

* * * * *